(12) United States Patent
Liao et al.

(10) Patent No.: US 9,186,087 B2
(45) Date of Patent: Nov. 17, 2015

(54) COMBINED CARDIAC AND RESPIRATORY MOTION COMPENSATION FOR ATRIAL FIBRILLATION ABLATION PROCEDURES

(75) Inventors: Rui Liao, Princeton Junction, NJ (US); Alexander Benjamin Brost, Erlangen (DE); Wen Wu, East Windsor, NJ (US); Terrence Chen, Princeton, NJ (US); Joachim Hornegger, Effeltrich (DE); Martin Willibald Koch, Nürnberg (DE); Norbert Strobel, Heroldsbach (DE); Andreas Wimmer, Forchheim (DE)

(73) Assignees: Siemens Aktiengesellschaft, Munich (DE); Friedrich-Alexander-Universität Erlangen-Nürnberg, Erlangen (DE)

( * ) Notice: Subject to any disclaimer, the term of this patent is extended or adjusted under 35 U.S.C. 154(b) by 470 days.

(21) Appl. No.: 13/433,817

(22) Filed: Mar. 29, 2012

(65) Prior Publication Data

US 2013/0331687 A1    Dec. 12, 2013

Related U.S. Application Data

(60) Provisional application No. 61/475,015, filed on Apr. 13, 2011.

(51) Int. Cl.
| | |
|---|---|
| *A61B 5/06* | (2006.01) |
| *A61B 6/12* | (2006.01) |
| *A61B 6/00* | (2006.01) |
| *A61B 19/00* | (2006.01) |
| *A61B 17/00* | (2006.01) |

(52) U.S. Cl.
CPC . *A61B 5/061* (2013.01); *A61B 6/12* (2013.01); *A61B 6/487* (2013.01); *A61B 6/5217* (2013.01); *A61B 6/503* (2013.01); *A61B 6/504* (2013.01); *A61B 2017/00699* (2013.01); *A61B 2017/00703* (2013.01); *A61B 2019/5238* (2013.01); *A61B 2019/5265* (2013.01)

(58) Field of Classification Search
CPC ............ A61B 5/00; A61B 5/06; A61B 5/065; A61B 2017/00694; A61B 2017/00699; A61B 2017/00703; A61B 19/5244
USPC .................................................. 600/407, 425
See application file for complete search history.

(56) References Cited

U.S. PATENT DOCUMENTS

| | | | |
|---|---|---|---|
| 6,162,174 A * | 12/2000 | Friemel | 600/447 |
| 2008/0319297 A1 * | 12/2008 | Danehorn | 600/373 |

OTHER PUBLICATIONS

Robust Learning-Based Detection and Tracking of Coronary Sinus (CS) Catheter Electrodes to Assist Atrial Fibrillation (AB) Treatment filed Sep. 12, 2011; U.S. Appl. No. 13/229,855.

* cited by examiner

*Primary Examiner* — Peter Luong

(57) ABSTRACT

A method for compensating cardiac and respiratory motion in atrial fibrillation ablation procedures includes (a) simultaneously determining a position of a circumferential mapping (CFM) catheter and a coronary sinus (CS) catheter in two consecutive image frames of a series of first 2-D image frames; (b) determining a distance between a virtual electrode on the CS catheter and a center of the CFM catheter for a first image frame of the two consecutive image frames, and for a second image frame of the two consecutive image frames; and (c) if an absolute difference of the distance for the first image frame and the distance for the second image frame is greater than a predetermined threshold, compensating for motion of the CFM catheter in a second 2-D image.

24 Claims, 8 Drawing Sheets

| Displacement Detection | | | | | | | | |
|---|---|---|---|---|---|---|---|---|
| | | 2% | 5% | 6% | 7% | 10% | 15% | 20% |
| VE | FP | 22.7 % | 5.8 % | 4.2 % | 2.7 % | 0.5 % | 0.0 % | 0.0 % |
| | FN | 0.0 % | 0.0 % | 14.3 % | 57.1 % | 42.9 % | 57.1 % | 85.7 % |

COMBINED CARDIAC AND RESPIRATORY MOTION COMPENSATION FOR ATRIAL FIBRILLATION ABLATION PROCEDURES

CROSS REFERENCE TO RELATED UNITED STATES APPLICATIONS

This application claims priority from "Combined Cardiac and Respiratory Motion Compensation for Atrial Fibrillation Ablation Procedures", U.S. Provisional Application No. 61/475,015 of Liao, et al., filed Apr. 13, 2011, the contents of which are herein incorporated by reference in their entirety.

TECHNICAL FIELD

This disclosure is directed to methods for combined cardiac and respiratory motion compensation in digitized fluoroscopy images used to guide catheter ablation procedures.

DISCUSSION OF THE RELATED ART

Atrial fibrillation (AFib) is widely recognized as a leading cause of stroke. Within the last years, the treatment of atrial fibrillation has gained more and more importance. An increasingly popular treatment option for AFib is catheter ablation during which the pulmonary veins attached to the left atrium (LA) are electrically isolated. These procedures are performed in electrophysiology (EP) labs usually equipped with modern C-arm X-ray systems providing 3-D imaging of the heart. Due to the rather low soft tissue contrast of X-ray imaging, the heart is not visible in these images. The use of fluoroscopic overlay images, perspectively rendered from 3-D data sets, makes it possible to augment live 2-D X-ray projections with soft-tissue information. However, catheter navigation using augmented fluoroscopy may be compromised by cardiac and respiratory motion. One approach to overcome this effect, by providing a motion compensated overlay, involves tracking of a commonly used circumferential mapping (CFM) catheter which has been firmly positioned at the ostium of the pulmonary vein in simultaneous biplane images. However, this method cannot detect when the CFM catheter is moving from one PV to another.

Another method tracks a catheter placed in the coronary sinus (CS) vein for respiratory motion compensation. However, the CS catheter is far from the site of ablation and it is unclear if the motion obtained from the CS catheter can be directly used for motion compensation, in particular, considering simultaneous compensation for both cardiac and respiratory motion. In addition, there are two other issues with using the CS catheter for motion compensation. First, the correlation between the observed CS catheter motion and the actual motion required for dynamic overlay may be low. Second, the catheter in the coronary sinus may not always be visible due to collimation to reduce X-ray dose.

SUMMARY

Exemplary embodiments of the invention as described herein generally include methods and systems for combined cardiac and respiratory motion compensation that use the CS catheter as a point of reference to detect when the circumferential mapping catheter is moved from one PV to another, and derive while the motion estimate for adapting the fluoroscopic overlay by localizing the circumferential mapping catheter. A virtual electrode (VE) placed on the CS catheter more proximal than any other electrode is used to obtain a good anchor point along the CS catheter. An algorithm according to an embodiment of the invention that uses both the CS catheter and the mapping catheter can detect non-physiological motion of the mapping catheter with a false positive rate of 4.2% and a false negative rate of 14.3%.

According to an aspect of the invention, there is provided a method for compensating cardiac and respiratory motion in atrial fibrillation ablation procedures, including (a) simultaneously determining a position of a circumferential mapping (CFM) catheter and a coronary sinus (CS) catheter in two consecutive image frames of a series of first 2-D image frames; (b) determining a distance between a virtual electrode on the CS catheter and a center of the CFM catheter for a first image frame of the two consecutive image frames, and for a second image frame of the two consecutive image frames; and (c) if an absolute difference of the distance for the first image frame and the distance for the second image frame is greater than a predetermined threshold, compensating for motion of the CFM catheter in a second 2-D image.

According to a further aspect of the invention, the method includes repeating steps (a), (b), and (c) for each pair of consecutive image frames of the series of first 2-D image frames.

According to a further aspect of the invention, determining a position of the circumferential mapping (CFM) catheter comprises receiving a model of the CFM catheter determined from a set of points extracted from a first image frame of the series of first 2-D image frames, where the set of points are connected as a B-spline, segmenting the CFM catheter in a region of interest in each subsequent image frame of the series of first 2-D image frames, processing a segmentation result for each subsequent image frame to calculate a distance map for each subsequent image frame that encodes for each pixel in the image frame a distance from that pixel to a nearest pixel of the segmented CFM catheter, and registering the CFM catheter model to the segmented CFM catheter in each subsequent image frame to determine an optimal translation vector between the CFM catheter and the segmented CFM catheter for each subsequent image frame.

According to a further aspect of the invention, a position of the region of interest in each subsequent image frame is determined from a center of the registered CFM catheter model in a previous image frame.

According to a further aspect of the invention, processing a segmentation result for each subsequent image frame comprises skeletonizing the segmentation result for each subsequent image frame and calculating the distance map of each subsequent image frame from the skelotonized segmentation result.

According to a further aspect of the invention, registering the CFM catheter model to the segmented CFM catheter in each subsequent image frame comprises minimizing a cost function $$\sum_i I_{DT,t}(q_i + r_t)$$

of the distance map to determine the optimal translation vector $\hat{r}_t$, where $I_{DT,t}$ is a distance map of a subsequent image t, $r_t$ is a pixel in the distance map, $q_i$ is a point on the CFM catheter model, and the sum is over all points on the CFM catheter model.

According to a further aspect of the invention, determining a position of the coronary sinus (CS) catheter comprises receiving a model of the CS catheter determined from a set of points extracted from a first image frame of the series of first 2-D image frames, where the CS catheter is modeled as a set of electrodes extending from a tip of the CS catheter to a most proximal electrode (MPE), and including a virtual electrode positioned at a most proximal location on the CS catheter, detecting the tip, electrodes, and body points of the CS catheter in each subsequent frame using trained classifiers, generating a set of hypotheses $v_t$ for locating the VE in each subsequent frame based on a location of the detected MPE, and determining a best hypothesis $\hat{v}_t$ for locating the VE in each subsequent frame by maximizing a posterior probability $P(v_t|I_0, \ldots, _t)$ of the hypotheses $v_t$ for the image frames $I_{0, \ldots, t}$.

According to a further aspect of the invention, the method includes providing the set of detected electrodes and tips at each subsequent frame to a non-maximal suppression stage to reduce a number of catheter electrodes or tip candidates prior to selecting a catheter electrode or tip candidates having highest scores.

According to a further aspect of the invention, generating a set of hypotheses $v_t$ for locating the VE in each subsequent frame includes generating a seed hypothesis $\bar{v}_t$ for localizing the VE for a current time step t∈N by translating a VE position from a previous frame, $\hat{v}_{t-1}$, to a position of the most proximal electrode, $m_{MPE}$ for the current time step, and generating a set of tracking hypotheses $v_t$ from an affine transformation $$v_t = \begin{pmatrix} R & t \\ 0^T & 1 \end{pmatrix} \cdot \bar{v}_t,$$

with R∈$R^{2\times2}$, t∈$R^2$ being the parameter of the affine transformation, and where $m_{MPE}$ is a transformation center of the affine transformation.

According to a further aspect of the invention, the posterior probability $P(v_t|I_0, \ldots, _t)$ for an image frame t is a product of a likelihood term $P(I_t|v_t)$, a prediction term, $P(v_t|v_{t-1})$, and a posterior probability $P(v_{t-1}|I_0, \ldots, _t)$ for a previous image frame t−1, where the likelihood term $P(I_t|v_t)$ is estimated by combining a VE detection probability and a VE location matching.

According to another aspect of the invention, there is provided a method for compensating cardiac and respiratory motion in atrial fibrillation ablation procedures, including (a) simultaneously determining a position of a circumferential mapping (CFM) catheter and a coronary sinus (CS) catheter in two consecutive image frames of a series of first 2-D image frames, where determining a position of the circumferential mapping (CFM) catheter comprises registering a CFM catheter model to a segmented CFM catheter in each image frame to determine an optimal translation vector between the CFM catheter and the segmented CFM catheter for each image frame, and determining a position of the coronary sinus (CS) catheter comprises determining a best hypothesis $\hat{v}_t$ for locating a virtual electrode (VE) positioned at a most proximal location on the CS catheter in each frame by maximizing a posterior probability $P(v_t|I_0, \ldots, _t)$ of a set of tracking hypotheses $v_t$ for the VE for the image frames $I_{0, \ldots, t}$.

According to a further aspect of the invention, the method includes (b) determining a distance between a virtual electrode on the CS catheter and a center of the CFM catheter for a first image frame of the two consecutive image frames, and for a second image frame of the two consecutive image frames, and (c) if an absolute difference of the distance for the first image frame and the distance for the second image frame is greater than a predetermined threshold, compensating for motion of the CFM catheter in a second 2-D image, where steps (a), (b), and (c) are repeated for each pair of consecutive image frames of the series of first 2-D image frames.

According to a further aspect of the invention, determining a position of the circumferential mapping (CFM) catheter includes receiving a model of the CFM catheter determined from a set of points extracted from a first image frame of the series of first 2-D image frames, where the set of points are connected as a B-spline, segmenting the CFM catheter in a region of interest in each subsequent image frame of the series of first 2-D image frames, and processing a segmentation result for each subsequent image frame to calculate a distance map for each subsequent image frame that encodes for each pixel in the image frame a distance from that pixel to a nearest pixel of the segmented CFM catheter, where registering the CFM catheter model to the segmented CFM catheter in each image frame comprises minimizing a cost function $$\sum_i I_{DT,t}(q_i + r_t)$$

of the distance map to determine the optimal translation vector $\hat{r}_t$, where $I_{DT,t}$ is a distance map of an image t, $r_t$ is a pixel in the distance map, $q_i$ is a point on the CFM catheter model, and the sum is over all points on the CFM catheter model.

According to a further aspect of the invention, determining a position of the coronary sinus (CS) catheter includes receiving a model of the CS catheter determined from a set of points extracted from a first image frame of the series of first 2-D image frames, where the CS catheter is modeled as a set of electrodes extending from a tip of the CS catheter to a most proximal electrode (MPE), and includes the virtual electrode (VE), detecting the tip, electrodes, and body points of the CS catheter in each subsequent frame using trained classifiers, and generating the set of tracking hypotheses $v_t$ for locating the VE in each subsequent frame based on a location of the detected MPE.

According to a further aspect of the invention, generating a set of tracking hypotheses $v_t$ for locating the VE in each subsequent frame includes generating a seed hypothesis $\bar{v}_t$ for localizing the VE for a current time step t∈N by translating a VE position from a previous frame, $\hat{v}_{t-1}$, to a position of the most proximal electrode, $m_{MPE}$ for the current time step, and generating a set of tracking hypotheses $v_t$ from an affine transformation $$v_t = \begin{pmatrix} R & t \\ 0^T & 1 \end{pmatrix} \cdot \bar{v}_t,$$

with R∈$R^{2\times2}$, t∈$R^2$ being the parameter of the affine transformation, and where $m_{MPE}$ is a transformation center of the affine transformation.

According to another aspect of the invention, there is provided a non-transitory program storage device readable by a computer, tangibly embodying a program of instructions executed by the computer to perform the method steps for compensating cardiac and respiratory motion in atrial fibrillation ablation procedures.

DETAILED DESCRIPTION OF EXEMPLARY EMBODIMENTS

Figure 1A:
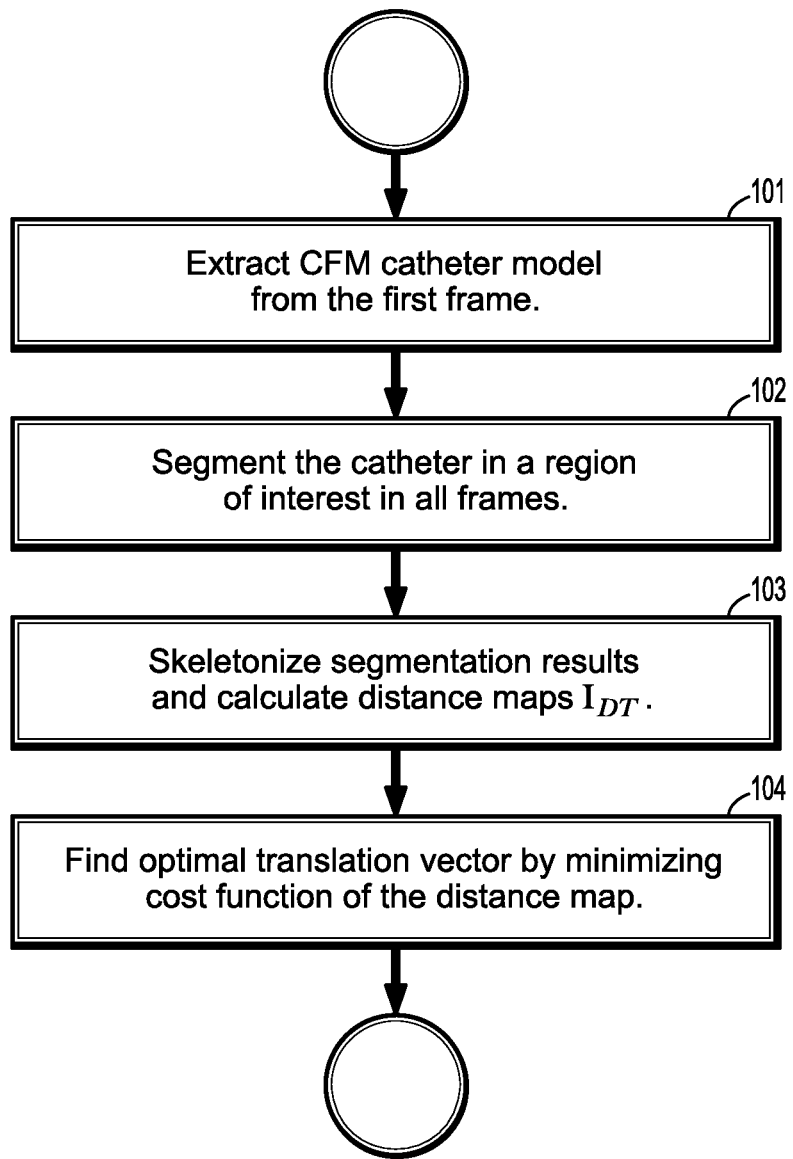
FIGS. 1A-C are flowcharts of motion compensation methods according to embodiments of the invention.

Exemplary embodiments of the invention as described herein generally include systems and methods for combined cardiac and respiratory motion compensation in fluoroscopic images. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-dimensional images and voxels for 3-dimensional images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to $R$ or $R^7$, the methods of the inventions are not limited to such images, and can be applied to images of any dimension, e.g., a 2-dimensional picture or a 3-dimensional volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

A motion compensation approach according to an embodiment of the invention involves tracking the CFM catheter as well as tracking a VE placed on the CS catheter. The absolute distance between the center of the CFM catheter and the VE is used to identify whether one of the catheters is moved by the physician or whether both catheters undergo physiological movements. A flowchart of a motion compensation approach according to an embodiment of the invention is presented in FIGS. 1A-C.

Circumferential Mapping Catheter Tracking

Referring now to FIG. 1A, according to an embodiment of the invention, a circumferential mapping catheter is initially extracted at step 101 from a 2-D X-ray image by manual interaction to provide an accurate 2-D catheter model for motion estimation. Input points are manually selected and connected as a B-spline. The manual interaction is used only for the first frame in a sequence of frames to generate the 2-D model which is then propagated throughout the remaining frames of the sequence.

Figure 2:
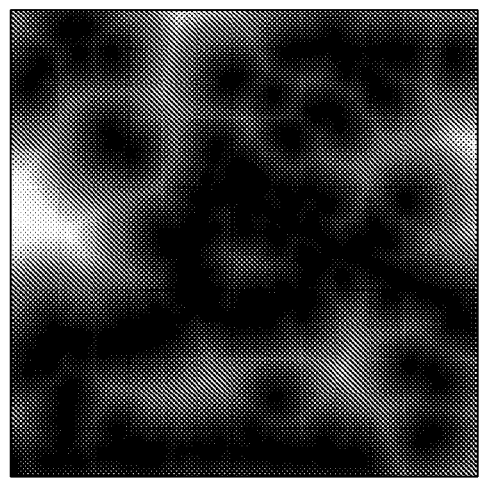
FIGS. 2(a)-(c) illustrate segmentation and processing of a catheter in an image frame, according to embodiments of the invention.
Figure 2:
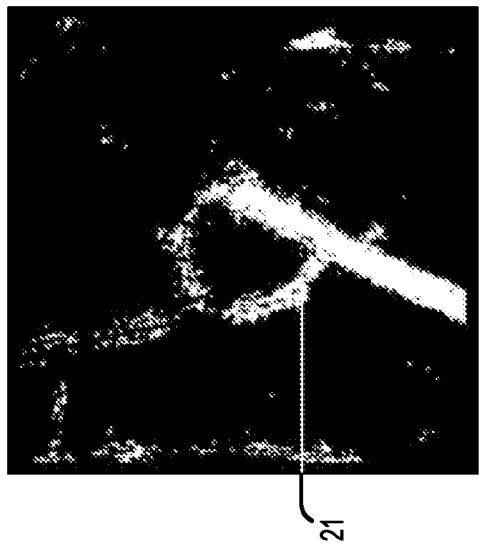
Figure 2:
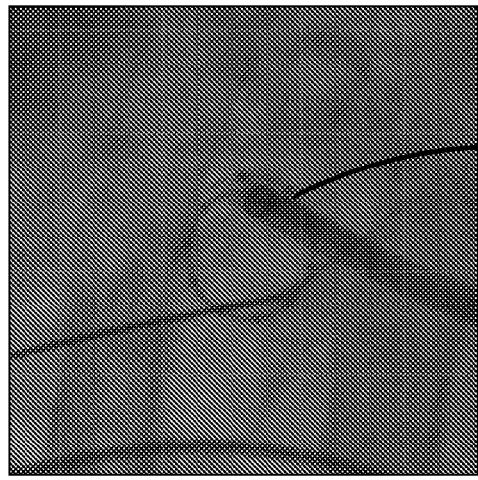

In each frame, the catheter is segmented at step 102 in a region of interest (ROI), as shown in FIG. 2(a). The catheter is indicated by reference number 21. The position of this region is determined by the center of the tracked catheter model from the previous frame. For catheter segmentation, Haar-like features and a cascade of boosted classifiers are used. Haar-like features calculate various patterns of intensity differences. To achieve reliable and fast segmentation, the most suitable features for discriminating between catheter and background are chosen and integrated into a classifier in a suitable manner. An exemplary, non-limiting method of building a classifier is the AdaBoost algorithm. AdaBoost build a strong classifier by adding a weak classifier that minimizes a classification error to a linear combination of weak classifiers until the overall error is below the desired threshold. After each training iteration, the importance of individual samples is re-weighted to put more emphasis on misclassifications for the next evaluation. Instead of single features and intensity thresholds, classification and regression trees (CARTs) are used as weak classifiers. Through this decomposition, flexibility is increased and objects with complex feature distributions can be handled. According to an embodiment of the invention, N strong classifiers composed of weighted combinations of CARTs are organized into a cascade. At each stage, a sample is either rejected or passed on to the next stage. Only if the sample is accepted at the final stage, it is assumed to belong to the target object, as shown in FIG. 2(b).

Catheter tracking according to an embodiment of the invention is performed by rigid registration of the 2-D catheter model to the segmentation result. To this end, the same ROI used for segmentation is considered. At step 103, a tracking approach according to an embodiment of the invention applies a thinning algorithm to the segmentation results that skeletonizes the segmentations, and then calculates, for each frame in the sequence of frames, a distance map $I_{DT,t}$ from the skeleton that encodes for each pixel the absolute distance from that pixel to its closest segmented catheter pixel, as shown in FIG. 2(c). The distance map also provides a smooth representation of the fluoroscopic image with a pronounced minimum around the shape of the mapping catheter to increase the capture range. The cost function for a combined registration-tracking approach according to an embodiment of the invention is based on the distance map $I_{DT,t}$. As a 2-D/2-D registration is used, the result is a 2-D pixel offset $r \in R^2$. According to an embodiment of the invention, rotation is not considered. The average distance between catheter model and segmentation derived from the fluoroscopic image is then considered as the cost value. The optimal translation vector $\hat{r}_t$ is found, at step 104, from minimizing the cost function:

$$\hat{r}_t = \operatorname{argmin}_{r_t} \sum_i I_{DT,t}(q_i + r_t), \tag{1}$$

where $q_i$ denotes a point on the catheter model. Optimization is performed for each frame using a nearest neighbor search. The estimated 2-D optimal translation vector $\hat{r}_t$ for each frame can be used for motion compensation of the frame.

Coronary Sinus Catheter Tracking

Figure 3:
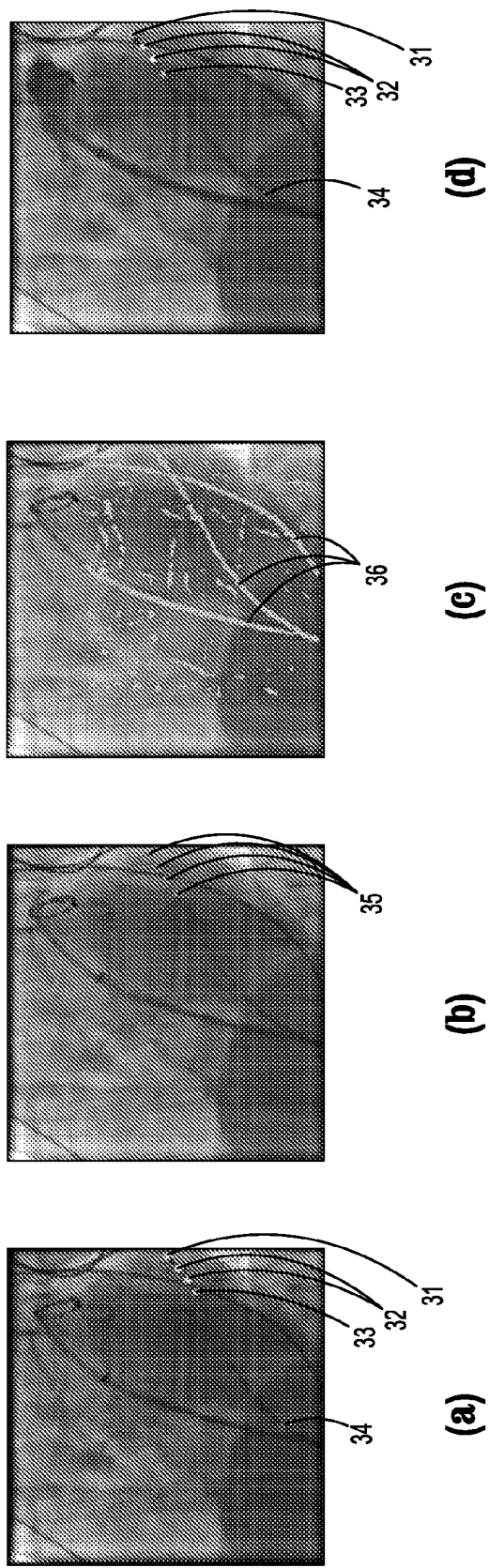
FIGS. 3(a)-(d) illustrates image processing of input data with user initialization, detected electrodes, detected body points and tracking results, according to embodiments of the invention.

The coronary sinus catheter is modeled as a set of electrodes, starting from the tip of the catheter going through each individual electrode including the most proximal electrode (MPE), to the virtual electrode (VE). FIG. 3(a) illustrates an example of a CS catheter, including the tip 31, the intermediate electrodes 32, and the MPE 33. The virtual electrode (VE) 34 is a reference point set by clicking on an arbitrary proximal position along the catheter shaft. The initial motivation to introduce the VE is to have a proximal reference point for observing breathing motion which is unaffected by heart beat.

Figure 1B:
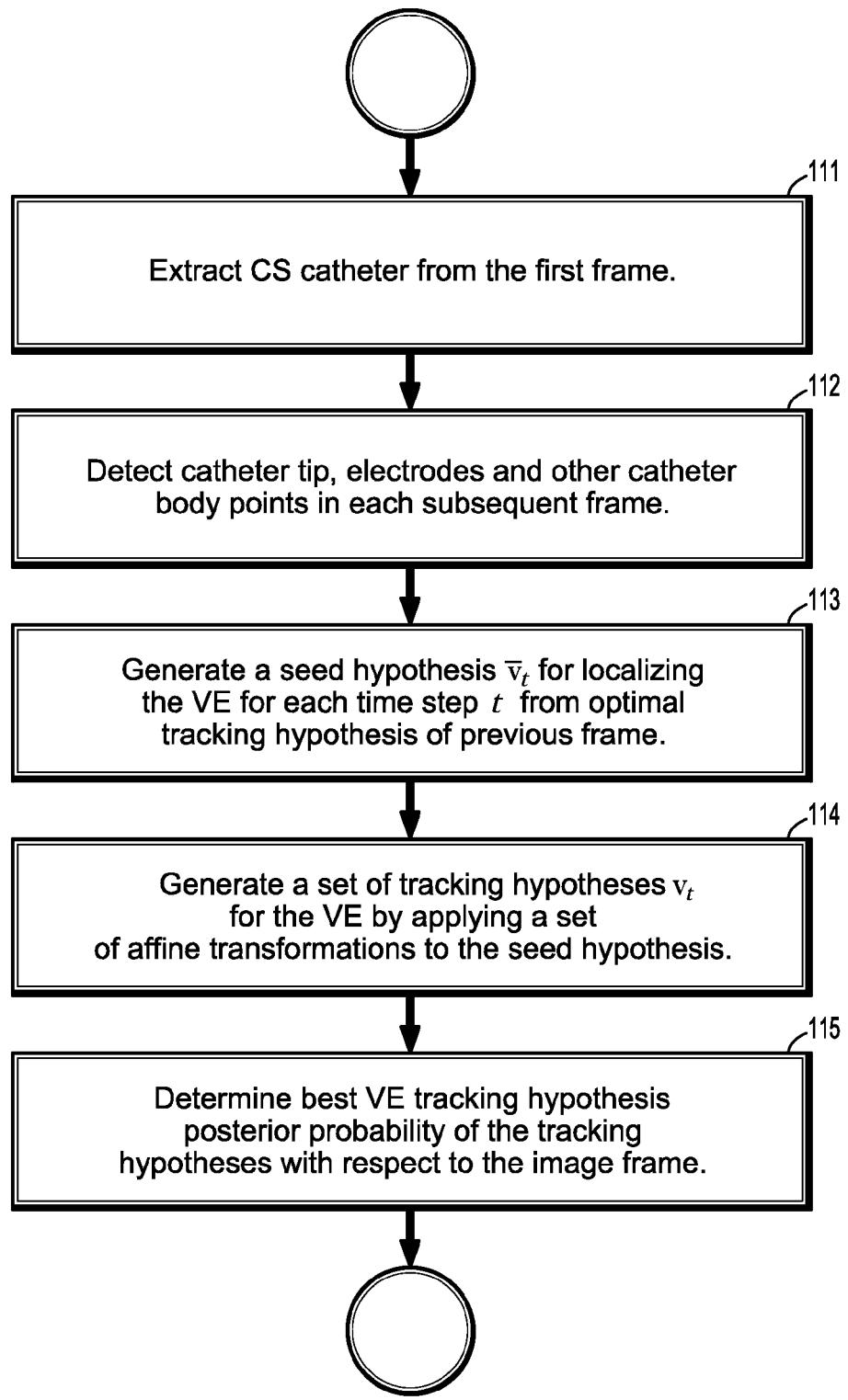

Referring now to FIG. 1B, at step 111, as with the circumferential mapping catheter, manual interaction is used to extract the initial CS catheter model from the first frame in a fluoroscopic sequence. For the remaining frames, all electrodes, including the virtual electrode, are tracked. The virtual electrode (VE) can also be used as a reference point to indicate whether the circumferential mapping catheter has changed positions from one PV to another. According to embodiments of the invention, the VE can be modeled by a set of image coordinates which are sampled along a spline between the MPE and the VE. The VE can also be associated with a template that represents a set of image intensity values associated with the VE model. The VE template is used when normalized cross correlation is computed between the VE template and a tracking hypothesis's patch.

According to an embodiment of the invention, tracking the virtual electrode includes two stages. In a first stage, all the real electrodes between the tip and the MPE are robustly tracked. In a second stage, the VE is inferred from the MPE along the CS catheter. Experiments indicated that the motion of the VE was more consistent with the circumferential mapping catheter motion than with the MPE or other electrodes on the CS catheter.

To track all the real electrodes, embodiments of the invention use learning-based detectors to generate hypotheses of possible displacement models. In embodiments of the invention, the catheter tip, electrodes and other catheter body points are detected at step 112 in each frame using trained classifiers that use Haar-like features and steerable features in a centered window. Each classifier is a Probabilistic Boosting Tree (PBT) that can output a probability. The set of detected electrodes and tips at each frame is provided to a non-maximal suppression stage to reduce the number of catheter electrode or tip candidates prior to selecting the catheter electrode or tip candidates having the highest scores. Non-maximal suppression is a technique for clustering detection results that combines multiple candidates that are close together and should be considered as the same candidate.

According to embodiments of the invention, all the classifiers are trained from a plurality of manually annotated frames. In one exemplary, non-limiting embodiment, 5103 frames are used for training. Specially-designed hypotheses generated by a number of learning-based detectors are fused. Robust hypothesis matching through a Bayesian framework is then used to select the best displacement hypothesis for each frame. These classifier training techniques are described in "Robust Learning-Based Detection and Tracking of Coronary Sinus (CS) Catheter Electrodes to Assist Atrial Fibrillation (AB) Treatment", application Ser. No. 13/229,855, filed on Sep. 12, 2011, the contents of which are herein incorporated by reference in their entirety.

Given an MPE robustly localized in the first stage, hypotheses for tracking the VE are generated automatically in the second stage. The set of hypotheses is generated from the VE model by parametrically manipulating the VE location based on the MPE location. The scheme works as follows. At step 113, a seed hypothesis $\bar{r}_t$ for detecting the YE is generated from the VE model for time step t∈N by translating $\hat{v}_{t-1}$, a set of 2-D image points from the previous image frame in homogeneous coordinates that represent the optimal tracking hypothesis for that frame, to the position of the most proximal electrode, $m_{MPE}$. From the seed hypothesis, the $m_{MPE}$ is considered as the transformation center and a set of affine transformation are applied to generate, at step 114, a set of tracking hypotheses $v_t$:

$$v_t = \begin{pmatrix} R & t \\ 0^T & 1 \end{pmatrix} \cdot \bar{v}_t, \quad (2)$$

with $R \in R^{2 \times 2}$ and $t \in R^2$ being the parameter of the affine transformation expressed by EQ. (2). This strategy is efficient in generating a near-complete set of tracking hypotheses. Then, at step 115, a best VE tracking hypothesis for each frame is determined by maximizing the posterior probability P:

$$\hat{v}_t = \arg\max_{v_t} P(v_t | I_0, \ldots, t), \quad (3)$$

with $I_{0, \ldots, t}$ representing the images from time 0 to time t. Note that not all of the images from time 0 to time t need be taken into account, as long at least one previous result is used. This equation defines a maximization of the posterior probability which assumes a Markovian representation of the VE motion. The posterior probability includes two parts: a likelihood $P(I_t|v_t)$ and a prediction term, $P(v_t|v_{t-1})$, and can be expressed as: $P(v_t|I_{0,\ldots,t}) = P(I_t|v_t)P(v_t|v_{t-1})P(v_{t-1}|I_{0,\ldots,t})$, where $P(v_{t-1}|I_{0,\ldots,t})$ is the posterior probability for the previous image frame t−1. The likelihood term $P(I_t|v_t)$ is estimated by combining the VE detection probability and the VE's template matching. The prediction term $P(v_t|v_{t-1})$ captures motion smoothness. The VE tracking hypothesis for each frame from EQ. (3) can be used to update the VE template from the previous frame to the current frame. Thus, information from all previous frames can be used.

FIGS. 3(a)-(d) shows an example of input data with user initialization, detected electrodes, detected body points and tracking results. FIG. 3(a) shows a fluoroscopic image with user inputs, i.e., four electrodes and the VE, as described above. FIG. 3(b) shows the automatically detected electrode positions 35 after the non-maximal suppression, without a decision as to which electrode is the tip and which electrodes belong to the body. FIG. 3(c) shows detected catheter body points 36 (for clarity, only the larger body parts are indicated), and FIG. 3(d) shows the tracked electrodes 31, 32, 33, and VE 34.

Displacement Detection

According to an embodiment of the invention, motion compensation is performed by tracking the circumferential mapping (CFM) catheter, as the motion of the coronary sinus catheter is insufficiently correlated to estimate the motion of the PV ostium. This could be expected as the CS catheter, placed in the coronary sinus vein, lies between the left atrium and the left ventricle. As a result, its motion is influenced by the motion of the ventricle. The motion of the circumferential mapping catheter, on the other hand, is restricted because the left atrium is connected to the lungs via the pulmonary veins. However, the CS is useful as an anchor for detecting if the CFM catheter has moved from one PV ostium to the next. Embodiments of the invention assume that the absolute distance between the CS catheter and the CFM catheter remains sufficiently stable to classify whether the CFM catheter has moved away from its PV ostium.

Figure 1C:
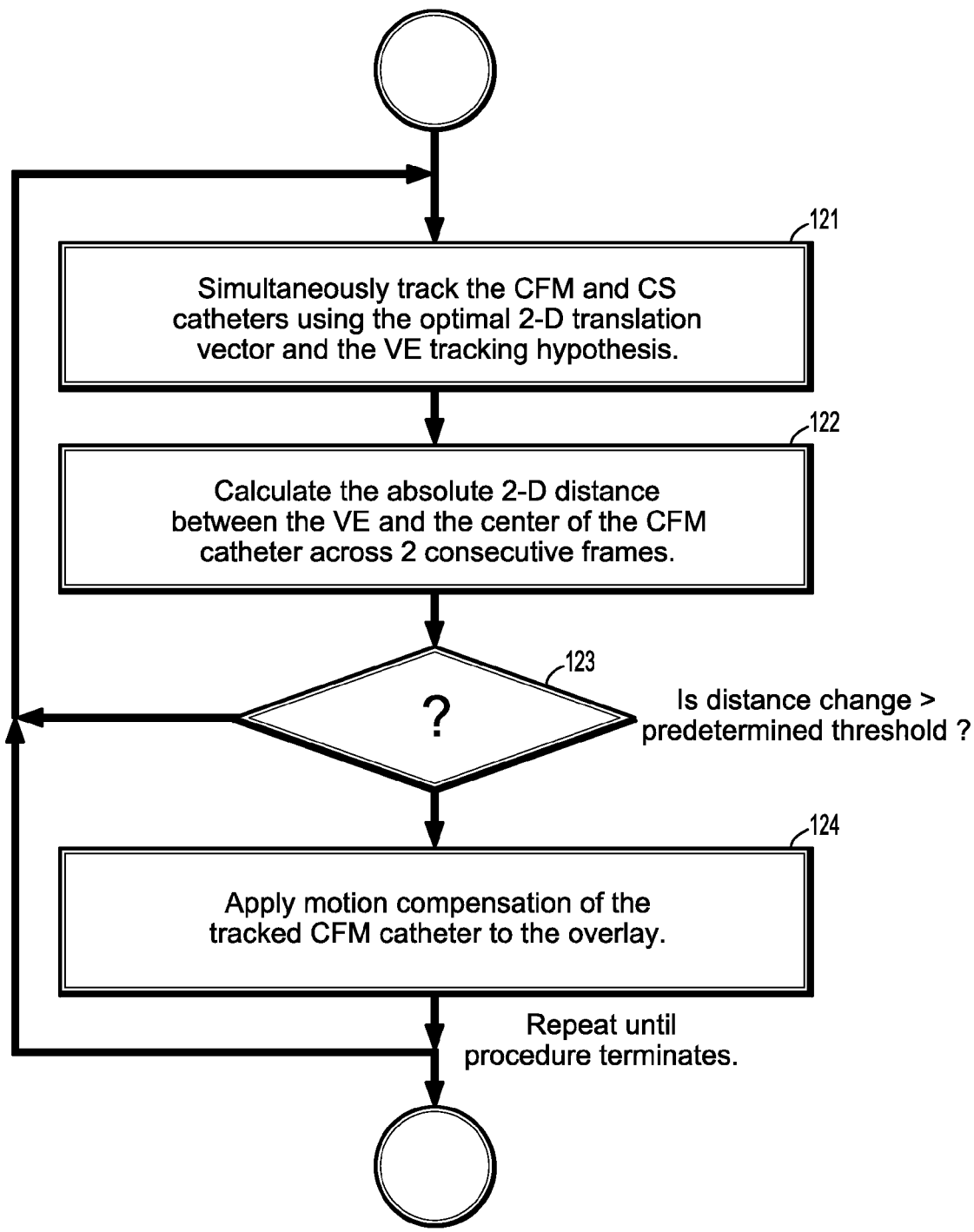

Referring now to FIG. 1C, to achieve a reliable and robust motion compensation, at step 121, embodiments of the invention track both the CFM catheter and the CS catheter simultaneously, using the estimated 2-D optimal translation vector from EQ. (1) and the VE tracking hypothesis from EQ. (3), and, at step 122, calculate the absolute 2-D distance between the VE and the center of the CFM catheter for two consecutive frames. If, at step 123, the distance change across the two consecutive frames is greater than a predetermined threshold percentage, it is assumed that the CFM catheter has moved from one pulmonary vein to another. In this case, no motion compensation is applied to the overlay images. However, even if no motion compensation is carried out, catheter tracking is still performed, at step 121. As soon as the absolute distance becomes stable again, e.g., the distance change is less than the predetermined threshold percentage, for example 6%, motion compensation of the tracked CFM catheter is then again applied to the fluoroscopic overlay at step 124, after which tracking is performed again, at step 121, until the procedure terminates.

Evaluation and Results

Methods according to embodiments of the invention were evaluated on 14 clinical data sets from two different hospitals and from 10 different patients. During three of these sequences, a 10-electrode CS catheter was used. In the remaining data sets, 4-electrode catheters were chosen. The images were either 512×512 pixels or 1024×1024 pixels. The pixel spacing varied between 0.173 pixel/mm to 0.345 pixel/mm. Image acquisition was performed without using ECG-triggered fluoroscopy. Hence, both respiratory and cardiac motion were present.

Figure 4A:
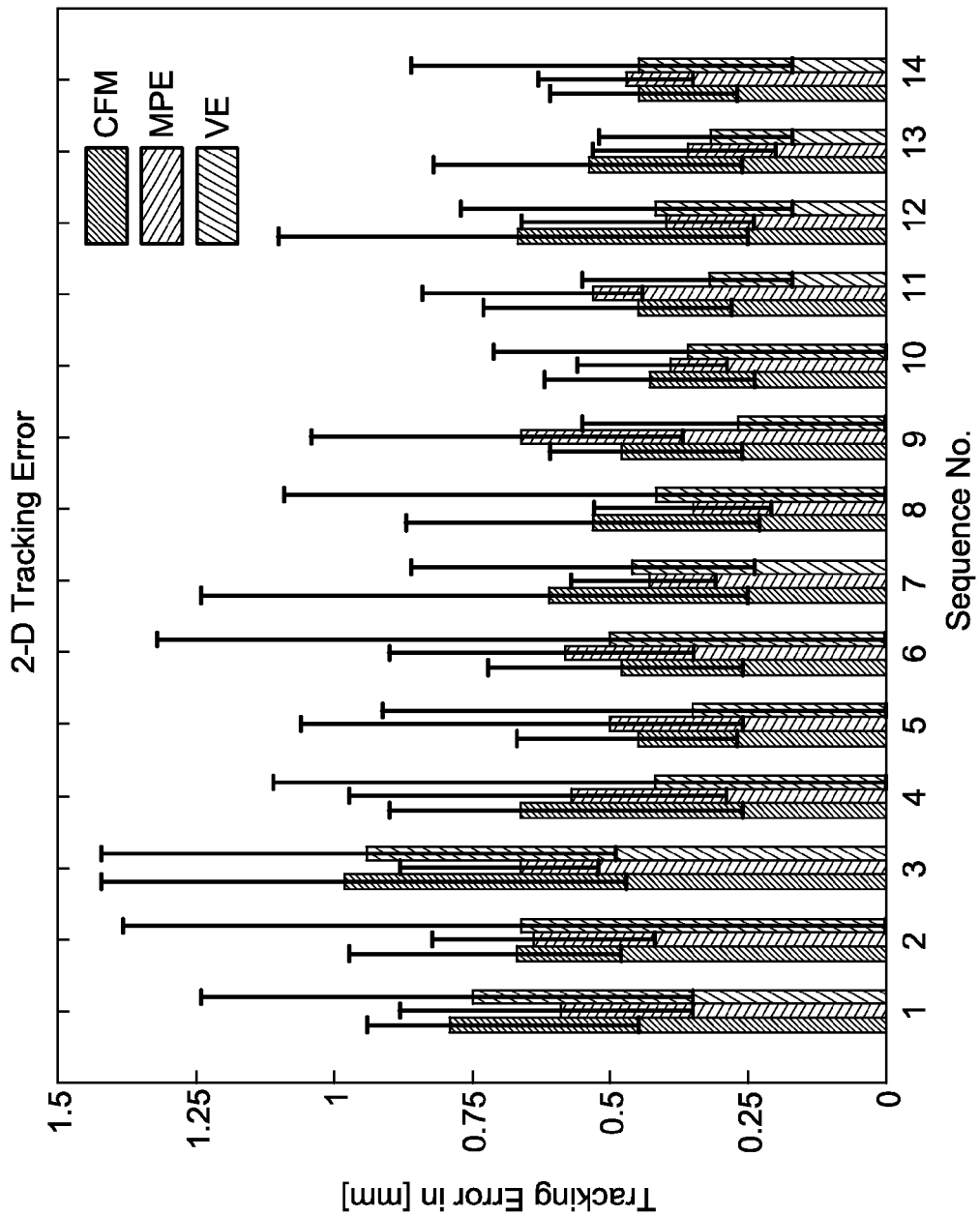
FIGS. 4(a)-(b) illustrates the accuracy of catheter tracking methods for the CFM catheter and the MPE and VE on the CS catheter, according to embodiments of the invention.

At first, the accuracy of the tracking methods was evaluated. The error for the tracking of the CFM catheter was calculated by considering the 2-D Euclidean distance to a gold-standard segmentation of the tip of the circumferential mapping catheter. The gold-standard segmentation was manually generated for each frame in every sequence. The segmentation was supervised by an electro-physiologist. The accuracy of the coronary sinus catheter and the virtual electrode was calculated as the 2-D Euclidean distance to a gold-standard segmentation of the whole CS catheter. FIG. 4(a) illustrates the accuracy (with standard deviation indicted by the black bars) for the catheter tracking methods for, in the order shown for each sequence number, the CFM catheter, the MPE on the CS catheter, and the VE on the CS catheter. The CFM tracking yielded an average 2-D error of 0.55 mm, which includes the inherent model error. The tracking of the MPE on the CS catheter yielded an average 2-D tracking error of 0.52 mm. A gold-standard segmentation of the CS catheter was used for evaluation. The VE tracking yielded an average 2-D tracking error of 0.49 mm.

Figure 4B:
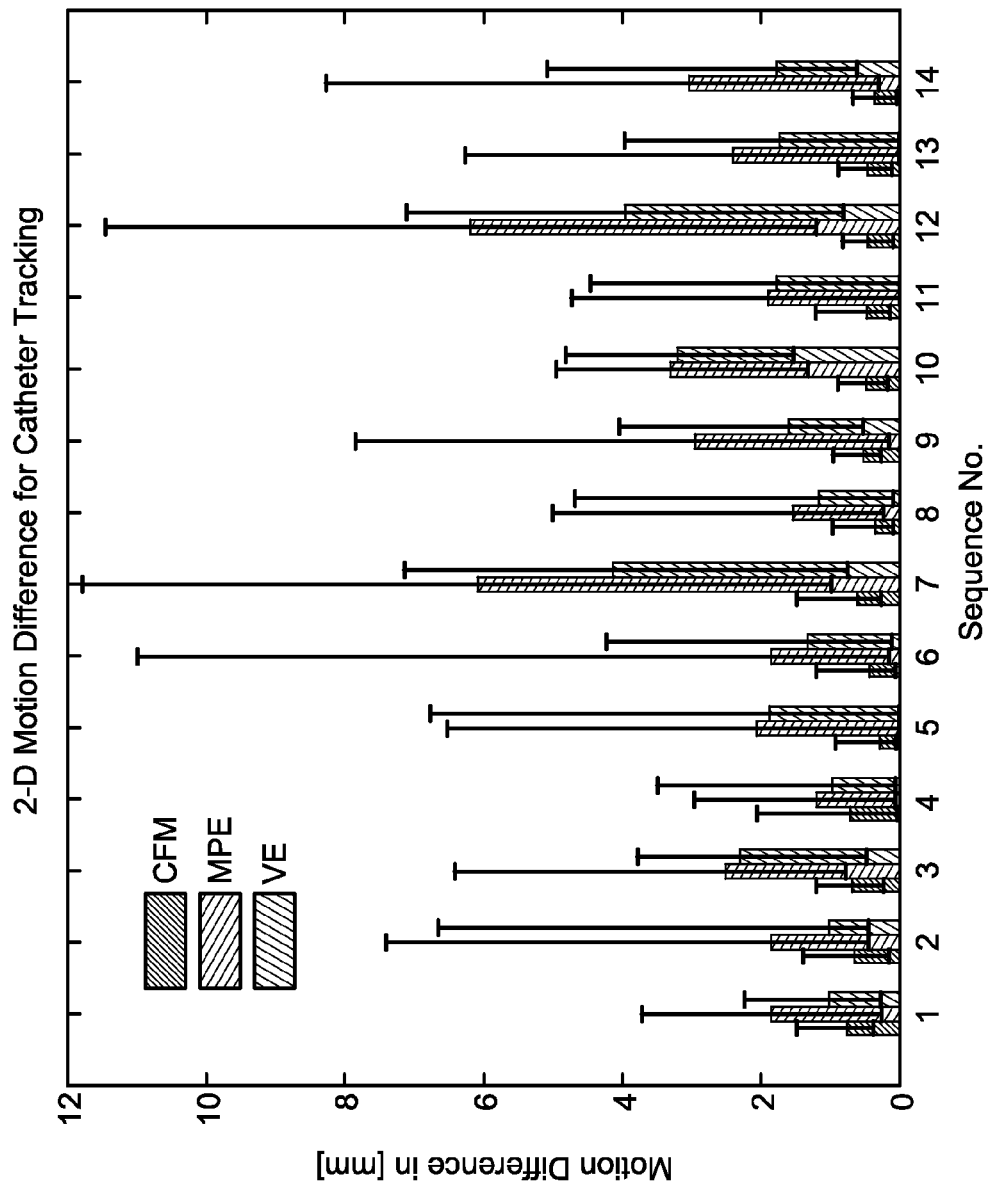

In addition, the motion obtained from the three tracking methods was compared to the motion observed at the PV ostia. This motion was obtained by using a gold-standard segmentation of the CFM catheter. The center of the catheter loop was used to calculate the underlying motion of the PV. FIG. 4(b) illustrates the differences between (with standard deviation indicted by the black bars) the catheter tracking methods for, in the order shown for each sequence number, the CFM catheter, the MPE on the CS catheter, and the VE on the CS catheter and the observed motion of the CFM catheter. The motion obtained by the CFM catheter differs on average by about 0.48 mm from the real motion, whereas the motion from the MPE had a mean error of about 2.61 mm. Using the VE, the mean error can be reduced from 2.61 mm to 1.68 mm. The maximum difference yielded by the CFM catheter was 2.06 mm, whereas the MPE was off by up to 11.80 mm and the VE by up to 7.14 mm. The 14 fluoroscopic sequences used for evaluating the tracking performance had the CFM catheter firmly placed at a single pulmonary vein, i.e., the CFM catheter did not move from one PV to the next.

To evaluate displacement detection methods according to embodiments of the invention, five further sequences were added to the data set. To detect CFM catheter displacement, a displacement threshold was introduced. The displacement threshold is a percentage of the distance between the VE and the center of the loop representing the CFM catheter. Results for different displacement thresholds using the absolute difference between the circumferential mapping catheter and the virtual electrode on the CS catheter are given in the table of FIG. 5. False positive (FP) is the percentage of wrongly detected motion and false negative (FN) is the percentage of undetected motion. The best result for displacement detection was found for an allowed change of the distance between 5% and 10%. A change in the absolute distance of 6% turned out to be the best threshold for detecting the real catheter motion in these experiments. In this case, the rate of false positive was 4.2% and the rate of false negative was 14.3%. Embodiments of the invention use the VE for displacement detection, because it can be a more stable reference than the MPE. This can be seen, e.g., by observing the mean errors and maximum differences shown in FIG. 4(b).

The results indicate that tracking algorithms according to embodiments of the invention are accurate enough to meet clinical needs, as shown in FIG. 4(a). However, only the tracking of the CFM catheter was found to be sufficiently accurate to be used for motion compensation without the need for a more sophisticated motion model, as shown in FIG. 4(b). Although the CS catheter did not provide a satisfying means for motion compensation, it can be used to detect displacement of the CFM catheter. If the distance between the CFM catheter and the VE changes by a predetermined amount, embodiments of the invention assume that the mapping catheter has moved from one pulmonary vein to another.

The tracking of the CFM catheter yielded an overall average error of 0.55 mm. Since this error also contains some model error of the underlying B-spline catheter model, which is not adapted over time, the actual tracking performance of the distance-transform-based method is even better. The motion difference between the real motion at the PV ostia and the estimated motion yielded a maximum error of 2.06 mm. The same error for the MPE was 11.80 mm and 7.14 mm for the VE, respectively. From these numbers, one can conclude that the CFM catheter is the best surrogate for the motion of the left atrium. Furthermore, the motion obtained from the CS catheter may be misleading.

Algorithms according to embodiments of the invention were applied to data affected by both cardiac and respiratory motion, but did not take into account the magnification factor of the C-arm system. Assuming a C-arm magnification factor of 1.5, a 2-D error of 0.55 mm at the detector corresponds to an error of around 0.37 mm at the iso-center. From the experiments, the detection of the moving CFM catheter using the absolute distance between the CFM and the VE yielded the best results. A change in the absolute distance of 6% was the best threshold for detecting displacement of the CFM catheter in the experiments. In this case, the rate of false positive was 4.2% and the rate of false negative was 14.3%. Compared to a mis-detection which may lead to incorrect overlay, a false detection is preferred, which would at most result in a few frames without motion correction. In the case of ECG-triggered fluoroscopy, a smaller displacement threshold could be used as image acquisition is always performed at roughly the same cardiac phase.

System Implementations

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figures 5, 6:
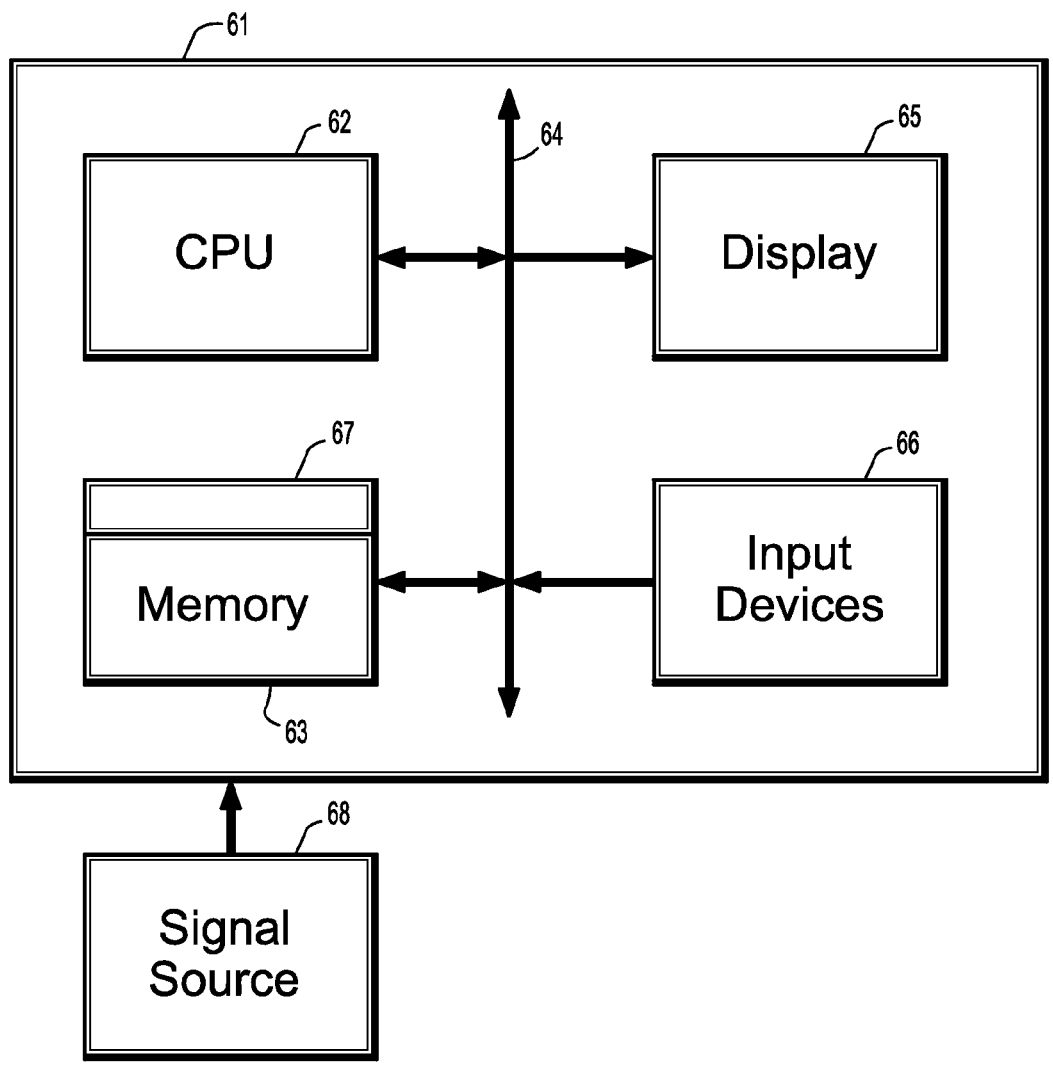
FIG. 5 is a table of results for different displacement thresholds using the absolute difference between the circumferential mapping catheter and the virtual electrode on the CS catheter, according to embodiments of the invention.
FIG. 6 is a block diagram of an exemplary computer system for implementing a method for combined cardiac and respiratory motion compensation in fluoroscopic images, according to an embodiment of the invention.

FIG. 6 is a block diagram of an exemplary computer system for implementing a method for combined cardiac and respiratory motion compensation in fluoroscopic images according to an embodiment of the invention. Referring now to FIG. 6, a computer system 61 for implementing the present invention can comprise, inter alia, a central processing unit (CPU) 62, a memory 63 and an input/output (I/O) interface 64. The computer system 61 is generally coupled through the I/O interface 64 to a display 65 and various input devices 66 such as a mouse and a keyboard. The support circuits can include circuits such as cache, power supplies, clock circuits, and a communication bus. The memory 63 can include random access memory (RAM), read only memory (ROM), disk drive, tape drive, etc., or a combinations thereof. The present invention can be implemented as a routine 67 that is stored in memory 63 and executed by the CPU 62 to process the signal from the signal source 68. As such, the computer system 61 is a general purpose computer system that becomes a specific purpose computer system when executing the routine 67 of the present invention.

The computer system 61 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A computer implemented method for compensating cardiac and respiratory motion in atrial fibrillation ablation procedures, the method executed by a computer comprising the step of:
   (a) acquiring a series of first 2-D image frames using an imaging system;
   (b) simultaneously determining a position of a circumferential mapping (CFM) catheter and a coronary sinus (CS) catheter in two consecutive frames of the series of first 2-D image frames;
   (c) determining a distance between a virtual electrode on the CS catheter and a center of the CFM catheter for a first consecutive image frame of the two consecutive image frames, and for a second consecutive image frame of the two consecutive image frames; and
   (d) if an absolute difference of the distance for the first consecutive image frame and the distance for the second consecutive image frame is greater than a predetermined threshold, compensating for motion of the CFM catheter in another 2-D image,
   wherein determining a position of the coronary sinus (CS) catheter comprises:
      receiving a model of the CS catheter determined from a set of points extracted from a first image frame of the series of first 2-D image frames, wherein said CS catheter is modeled as a set of electrodes extending from a tip of the CS catheter to a first proximal electrode (FPE), and including a virtual electrode (VE) positioned at a first proximal location on the CS catheter;
      detecting the tip, electrodes, and body points of the CS catheter in each subsequent frame using trained classifiers;
      generating a set of hypothesis $v_t$ for locating the VE in each subsequent frame based on a location of the detected FPE; and
      determining a hypothesis $\hat{v}_t$ for locating the VE in each subsequent frame by maximizing a posterior probability $P(v_t|I_0, \ldots, t)$ of the hypotheses $v_t$ for the image frames $I_0, \ldots, t$.

2. The method of claim 1, further comprising repeating steps (a), (b), (c), and (d) for each pair of consecutive image frames of the series of first 2-D image frames.

3. The method of claim 1, wherein determining a position of the circumferential mapping (CFM) catheter comprises:
   receiving a model of the CFM catheter determined from a set of points extracted from a first image frame of the series of first 2-D image frames, wherein said set of points are connected as a B-spline;
   segmenting the CFM catheter in a region of interest in each subsequent image frame of the series of first 2-D image frames;
   processing a segmentation result for each subsequent image frame to calculate a distance map for each subsequent image frame that encodes for each pixel in the image frame a distance from that pixel to a nearest pixel of the segmented CFM catheter; and
   registering said CFM catheter model to said segmented CFM catheter in each subsequent image frame to determine an optimal translation vector between the CFM catheter and the segmented CFM catheter for each subsequent image frame.

4. The method of claim 3, wherein a position of the region of interest in each subsequent image frame is determined from a center of the registered CFM catheter model in a previous image frame.

5. The method of claim 3, wherein processing a segmentation result for each subsequent image frame comprises skelotonizing the segmentation result for each subsequent image frame and calculating the distance map of each subsequent image frame from the skelotonized segmentation result.

6. The method of claim 3, wherein registering said CFM catheter model to said segmented CFM catheter in each subsequent image frame comprises minimizing a cost function $$\sum_i I_{DT,t}(q_i + r_t)$$

of the distance map to determine the optimal translation vector $\hat{r}_t$, wherein $I_{DT,t}$ is a distance map of a subsequent image t, $r_t$ is a pixel in said distance map, $q_i$ is a point on the CFM catheter model, and the sum is over all points on the CFM catheter model.

7. The method of claim 1, further comprising providing the set of detected electrodes and tips at each subsequent frame to a non-maximal suppression stage to reduce a number of catheter electrodes or tip candidates prior to selecting a catheter electrode or tip candidates having highest scores.

8. The method of claim 1, wherein generating a set of hypotheses $v_t$ for locating the VE in each subsequent frame comprises:
   generating a seed hypothesis $\bar{v}_t$ for localizing the VE for a current time step t∈N by translating a VE position from a previous frame, $\hat{v}_{t-1}$, to a position of the first proximal electrode, $m_{FPE}$ for the current time step; and
   generating a set of tracking hypotheses $v_t$ from an affine transformation $$v_t = \begin{pmatrix} R & t \\ 0^T & 1 \end{pmatrix} \cdot \bar{v}_t,$$

with R∈$R^{2\times2}$, t∈$R^2$ being the parameter of the affine transformation, and wherein $m_{FPE}$ is a transformation center of the affine transformation.

9. The method of claim 1, wherein said posterior probability $P(v_t|I_0, \ldots, _t)$ for an image frame t is a product of a likelihood term $P(I_t|v_t)$, a prediction term, $P(v_t|v_{t-1})$, and a posterior probability $P(v_{t-1}|I_0, \ldots, _t)$ for a previous image frame t−1, wherein said likelihood term $P(I_t|v_t)$ is estimated by combining a VE detection probability and a VE location matching.

10. A computer implemented method for compensating cardiac and respiratory motion in atrial fibrillation ablation procedures, the method executed by a computer comprising the steps of:
   (a) acquiring a series of first 2-D image frames using an imaging system;
   (b) simultaneously determining a position of a circumferential mapping (CFM) catheter and a coronary sinus (CS) catheter in two consecutive image frames of a series of first 2-D image frames; wherein
   determining a position of the circumferential mapping (CFM) catheter comprises registering a CFM catheter model to a segmented CFM catheter in each image frame to determine an optimal translation vector between the CFM catheter and the segmented CFM catheter for each image frame; and
   determining a position of the coronary sinus (CS) catheter comprises determining a hypothesis $\hat{v}_t$ for locating a virtual electrode (VE) positioned at a first proximal location on the CS catheter in each frame by maximizing a posterior probability $P(v_t|I_0, \ldots, _t)$ of a set of tracking hypotheses $v_t$ for the VE for the image frames $I_0, \ldots, _t$.

11. The method of claim 10, further comprising:
   (c) determining a distance between a virtual electrode on the CS catheter and a center of the CFM catheter for a first consecutive image frame of the two consecutive image frames, and for a second consecutive image frame of the two consecutive image frames; and
   (d) if an absolute difference of the distance for the first consecutive image frame and the distance for the second consecutive image frame is greater than a predetermined threshold, compensating for motion of the CFM catheter in another 2-D image,
   wherein steps (a), (b), (c), and (d) are repeated for each pair of consecutive image frames of the series of first 2-D image frames.

12. The method of claim 10, wherein determining a position of the circumferential mapping (CFM) catheter further comprises:
   receiving a model of the CFM catheter determined from a set of points extracted from a first image frame of the series of first 2-D image frames, wherein said set of points are connected as a B-spline;
   segmenting the CFM catheter in a region of interest in each subsequent image frame of the series of first 2-D image frames; and
   processing a segmentation result for each subsequent image frame to calculate a distance map for each subsequent image frame that encodes for each pixel in the image frame a distance from that pixel to a nearest pixel of the segmented CFM catheter,
   wherein registering said CFM catheter model to said segmented CFM catheter in each image frame comprises minimizing a cost function $$\sum_i I_{DT,t}(q_i + r_t)$$

of the distance map to determine the optimal translation vector $\hat{r}_t$, wherein $I_{DT,t}$ is a distance map of an image t, $r_t$ is a pixel in said distance map, $q_i$ is a point on the CFM catheter model, and the sum is over all points on the CFM catheter model.

13. The method of claim 10, wherein determining a position of the coronary sinus (CS) catheter further comprises:
   receiving a model of the CS catheter determined from a set of points extracted from a first image frame of the series of first 2-D image frames, wherein said CS catheter is modeled as a set of electrodes extending from a tip of the CS catheter to a first proximal electrode (FPE), and includes the virtual electrode (VE);
   detecting the tip, electrodes, and body points of the CS catheter in each subsequent frame using trained classifiers; and
   generating the set of tracking hypotheses $v_t$ for locating the VE in each subsequent frame based on a location of the detected FPE.

14. The method of claim 13, wherein generating a set of tracking hypotheses $v_t$ for locating the VE in each subsequent frame comprises:
   generating a seed hypothesis $\bar{v}_t$ for localizing the VE for a current time step t∈N by translating a VE position from a previous frame, $\hat{v}_{t-1}$, to a position of the first proximal electrode, $m_{FPE}$ for the current time step; and
   generating a set of tracking hypotheses $v_t$ from an affine transformation $$v_t = \begin{pmatrix} R & t \\ 0^T & 1 \end{pmatrix} \cdot \bar{v}_t,$$

with $R \in R^{2 \times 2}$, $t \in R^2$ being the parameter of the affine transformation, and wherein $m_{FPE}$ is a transformation center of the affine transformation.

15. A non-transitory program storage device readable by a computer, tangibly embodying a program of instructions executed by the computer to perform the method steps for compensating cardiac and respiratory motion in atrial fibrillation ablation procedures, the method comprising the steps of:
(a) acquiring a series of first 2-D image frames using an imaging system;
(b) simultaneously determining a position of a circumferential mapping (CFM) catheter and a coronary sinus (CS) catheter in two consecutive image frames of a series of first 2-D image frames; wherein
determining a position of the circumferential mapping (CFM) catheter comprises registering a CFM catheter model to a segmented CFM catheter in each image frame to determine an optimal translation vector between the CFM catheter and the segmented CFM catheter for each image frame; and
determining a position of the coronary sinus (CS) catheter comprises determining a hypothesis $\hat{v}_t$ for locating a virtual electrode (VE) positioned at a first proximal location on the CS catheter in each frame by maximizing a posterior probability $P(v_t | I_{0, \ldots, t})$ of a set of tracking hypotheses $v_t$ for the VE for the image frames $I_{0, \ldots, t}$.

16. The computer readable program storage device of claim 15, the method further comprising:
(c) determining a distance between a virtual electrode on the CS catheter and a center of the CFM catheter for a first consecutive image frame of the two consecutive image frames, and for a consecutive second image frame of the two consecutive image frames;
(d) if an absolute difference of the distance for the first consecutive image frame and the distance for the second consecutive image frame is greater than a predetermined threshold, compensating for motion of the CFM catheter in another 2-D image; and
repeating steps (a), (b), (c), and (d) for each pair of consecutive image frames of the series of first 2-D image frames.

17. The computer readable program storage device of claim 15, wherein determining a position of the circumferential mapping (CFM) catheter comprises:
receiving a model of the CFM catheter determined from a set of points extracted from a first image frame of the series of first 2-D image frames, wherein said set of points are connected as a B-spline;
segmenting the CFM catheter in a region of interest in each subsequent image frame of the series of first 2-D image frames; and
processing a segmentation result for each subsequent image frame to calculate a distance map for each subsequent image frame that encodes for each pixel in the image frame a distance from that pixel to a nearest pixel of the segmented CFM catheter.

18. The computer readable program storage device of claim 17, wherein a position of the region of interest in each subsequent image frame is determined from a center of the registered CFM catheter model in a previous image frame.

19. The computer readable program storage device of claim 17, wherein processing a segmentation result for each subsequent image frame comprises skeletonizing the segmentation result for each subsequent image frame and calculating the distance map of each subsequent image frame from the skeletonized segmentation result.

20. The computer readable program storage device of claim 17, wherein registering said CFM catheter model to said segmented CFM catheter in each subsequent image frame comprises minimizing a cost function $$\sum_i I_{DT,t}(q_i + r_t)$$

of the distance map to determine the optimal translation vector $\hat{r}_t$ wherein $I_{DT,t}$ is a distance map of a subsequent image t, $r_t$ is a pixel in said distance map, $q_i$ is a point on the CFM catheter model, and the sum is over all points on the CFM catheter model.

21. The computer readable program storage device of claim 15, wherein determining a position of the coronary sinus (CS) catheter comprises:
receiving a model of the CS catheter determined from a set of points extracted from a first image frame of the series of first 2-D image frames, wherein said CS catheter is modeled as a set of electrodes extending from a tip of the CS catheter to a first proximal electrode (FPE), and including the virtual electrode (VE) positioned at a most proximal location on the CS catheter;
detecting the tip, electrodes, and body points of the CS catheter in each subsequent frame using trained classifiers; and
generating a set of hypotheses $v_t$ for locating the VE in each subsequent frame based on a location of the detected FPE.

22. The computer readable program storage device of claim 21, the method further comprising providing the set of detected electrodes and tips at each subsequent frame to a non-maximal suppression stage to reduce a number of catheter electrodes or tip candidates prior to selecting a catheter electrode or tip candidates having highest scores.

23. The computer readable program storage device of claim 21, wherein generating a set of hypotheses $v_t$ for locating the VE in each subsequent frame comprises:
generating a seed hypothesis $\bar{v}_t$ for localizing the VE for a current time step $t \in N$ by translating a VE position from a previous frame, $\hat{v}_{t-1}$, to a position of the first proximal electrode, $m_{FPE}$ for the current time step; and
generating a set of tracking hypotheses $v_t$ from an affine transformation $$v_t = \begin{pmatrix} R & t \\ 0^T & 1 \end{pmatrix} \cdot \bar{v}_t,$$

with $R \in R^{2 \times 2}$, $t \in R^2$ being the parameter of the affine transformation, and wherein $m_{FPE}$ is a transformation center of the affine transformation.

24. The computer readable program storage device of claim 21, wherein said posterior probability $P(v_t | I_{0, \ldots, t})$ for an image frame t is a product of a likelihood term $P(I_t | v_t)$, a prediction term, $P(v_t | v_{t-1})$, and a posterior probability $P(v_{t-1} | I_{0, \ldots, t})$ for a previous image frame t−1, wherein said likelihood term $P(I_t | v_t)$ is estimated by combining a VE detection probability and a VE location matching.

* * * * *